US005427953A

United States Patent [19]

Yee

[11] Patent Number: 5,427,953

[45] Date of Patent: Jun. 27, 1995

[54] BLOOD TESTING METHOD

[75] Inventor: Hugh Y. Yee, Troy, Mich.

[73] Assignee: The Detroit Medical Center, Detroit, Mich.

[21] Appl. No.: 148,982

[22] Filed: Nov. 8, 1993

[51] Int. Cl.[6] .............................................. G01N 33/20

[52] U.S. Cl. ...................................... 436/74; 422/68.1; 436/73; 436/77; 436/166; 436/171; 436/182

[58] Field of Search ..................... 422/61, 68.1, 69, 73; 436/73, 74, 77, 164, 171, 177, 178, 182, 166

[56] References Cited

U.S. PATENT DOCUMENTS

| | | | |
|---|---|---|---|
| 3,708,228 | 1/1973 | Delves | 356/87 |
| 4,920,057 | 4/1990 | Castaneda | 436/77 |
| 5,019,516 | 5/1991 | Wiese | 436/77 |
| 5,217,594 | 6/1993 | Henkens et al. | 204/403 |
| 5,252,489 | 10/1993 | Macri | 436/87 |

*Primary Examiner*—Donald E. Czaja
*Assistant Examiner*—Lien Tran
*Attorney, Agent, or Firm*—Honigman Miller Schwartz and Cohn

[57] ABSTRACT

A method for testing blood samples for determining lead content therein. The method utilizes filter collection paper that is spotted with a blood sample; the blood sample spotted thereon is allowed to dry. The dried blood sample on the paper is punched out in a predefined manner to obtain a uniform volume equivalent to a predefined volume of whole blood. A dilute aqueous acid reagent containing a surfactant wetting agent is utilized to remove the part of the blood sample containing the lead. The filter collection paper retains the hemoglobin and blood proteins thus yielding a protein free solution that is suitable for direct analysis of the trace lead elements. The dried blood sample may be easily stored and economically transported to testing laboratories where the dried blood sample may be eluted into a hemoglobin and protein free solution that is stable for weeks under proper storage conditions. The method allows easy, economical and accurate testing of blood samples using standard analytical chemical measurement of trace elements such as lead.

4 Claims, 4 Drawing Sheets

BLOOD TESTING METHOD

BACKGROUND OF THE INVENTION

1. Field of the Invention

The present invention relates to collecting and analyzing blood samples and, more particularly, to a method and apparatus for collecting blood samples for determining the amount of heavy metals such as lead contained therein.

2. Description of the Related Technology

The Center for Disease Control ("CDC") in Atlanta has published new guidelines for preventing and treating lead poisoning in children. CDC is dropping the "threshold of concern" blood level from 25 to 10 micrograms per deciliter for children younger than age six, and is recommending direct blood lead measurement over the currently used erythrocyte protoporphyrin assay for detecting these lower lead levels.

Medical research has found that exposure to lead and consequent lead poisoning is devastating in developing children, especially from birth to six years of age. The investigation has disclosed that the currently acceptable blood lead level cut-off of twenty-five micrograms per deciliter still causes a significant decrease in the intelligence quotient (IQ) of children. The proposed 10 microgram per deciliter acceptable standard makes current screening methods for lead poisoning ineffective because of the lack of sensitivity. Currently, free erythrocyte protoporphyrin (FEP) and zinc protoporphyrin (ZPP) are commonly used mass screening methods of detecting lead poisoning. At 10 micrograms per deciliter of blood lead, the FEP and ZPP methods are not effective diagnostic measurements.

Testing blood for lead content is not, however, limited to just children. Workers exposed to lead in the work place must also be screened for excessive levels of lead in their blood. Testing of blood for lead content is generally considered the most incontrovertible evidence of lead absorption. Thus, there is need for blood testing of both children and adults for excessive lead levels in their blood.

Some of the currently used methods of blood lead analysis are graphite furnace atomic absorption spectrometry (GFAA), anodic stripping voltammetry (ASV), atomic absorption spectrometry (AAS) with methylisobutylketone (MIBK) extraction, and filter paper Delves cup (FPDC) with AAS. These blood lead analysis methods, however, each have their drawbacks.

GFAA provides a sensitive and accurate procedure for testing for lead content in blood, however, the GFAA-method requires expensive instrumentation and supplies such as graphite tubes.

The ASV method uses less expensive instrumentation but is still relatively slow and the instrument stability is difficult to maintain, especially at low concentrations of lead in the blood. Relatively long analysis time and expensive sample preparation materials make the ASV procedure cumbersome and unacceptably costly for large volume laboratories. The MIBK method requires two to four milliliters of blood and such a large sample volume is not desirable in screening programs for children.

A preferred method for blood lead testing is the FPDC which requires a small volume of blood and minimum sample preparation. A typical analysis time of 15 seconds for a sample is readily obtainable. The FPDC method is simple and rapid in processing and yields a sensitive, reproducible and accurate result.

The FPDC method utilizes filter collection paper that is spotted with a blood sample taken from a finger prick or earlobe puncture. The blood sample taken is of capillary blood from the surface of the skin and is of minimal amount. Blood from a vein is not required and the capillary blood drawn from the shallow skin prick is easily applied to the filter collection paper by spotting with a capillary tube (heparinized) that is used to collect the blood sample from the subject. A petri dish may be used to contain the filter collection papers and also to reduce the paper exposure when the blood is not being spotted onto the paper.

Once the filter collection paper is spotted with the blood sample, the paper is allowed to dry. The filter collection paper containing the dried blood sample may be stored in a glassine open-end envelope for transportation to the testing laboratory.

To analyze the blood sample, it is first necessary to obtain a disk of filter collection paper of an area which, when spotted with blood, holds a known volume of blood. A procedure to do this is more fully described in an article by Carl Vereby et al., *Rapid, Sensitive, Micro Blood Lead Analysis: A Mass Screening Technique for Lead Poisoning,* 15 *Journal of Analytical Toxicology* 237 (1991). This article describes a procedure for punching out the paper containing a dried blood sample. A hole punch is used to punch out one-quarter inch diameter disks that define a standard area of collection paper containing the dried blood sample. These punched out dried blood samples are next placed in a Delves cup and introduced into a high temperature means such as a flame. The collection paper ignites and burns creating an ash. This ash of paper and dried blood are then atomized by heating in a crucible of an atomic absorption spectrometer ("AAS") in which the lead concentration in the blood may be determined.

The AAS method for determining concentrations in blood samples is highly accurate for detection of lead in the 5–200 microgram per deciliter range, however, the burning of the paper to ash results in smoke and soot that carbonizes the heating crucible used to atomize the sample for testing in the AAS system. The resulting soot requires that the AAS system crucible be cleaned frequently, thereby increasing testing costs and slowing the number of tests that are possible in a given time period. In addition, when the paper is burned in the crucible, the formation of smoke from the paper burning tends to mask those spectral peaks which indicate the presence of trace amounts of lead.

What is needed is a method and apparatus which does not produce undesirable by-products that tend to mask the lead trace in the heated vapor, yet allows a simple, efficient and cost-effective means for testing lead concentration in blood samples utilizing a lead detection system such as, for example, an AAS system. It is therefore an object of the present invention to obtain the desired components of a blood sample containing lead in a solution that may be placed directly into a lead determining system, such as an AAS furnace, for spectral measurement of the lead atoms which may then be used to determine the amount of the lead concentration in a given volume of blood.

SUMMARY OF THE INVENTION

The present invention provides a method and system for collecting microliter samples of blood and determining lead content therein. The present invention accomplishes this by collecting whole blood from a subject and spotting this blood on collection paper. The spotted blood on the collection paper is dried. The dried blood spot is punched out into predefined area disks representing a known volume of whole blood. The disks of dried blood are eluted with a solution of dilute aqueous acid reagent containing a surfactant wetting agent that removes the blood components containing the lead from the blood spotted disks.

In an embodiment of the present invention, approximately a one-half inch diameter circle of dried whole blood is eluted into a volume of one milliliter solution to produce an equivalent of a 50 microliter volume of blood diluted 20 times. The filter collection paper retains the hemoglobin and blood proteins resulting in a protein free solution upon elution that is suitable for direct analysis of the lead contained in the blood. The eluting solution of the present invention is a dilute aqueous acid reagent containing a surfactant wetting agent, for example five percent volume per volume nitric acid with 0.75 percent volume per volume Triton X-100®. The dilute acid dissolves the blood components containing the trace elements of heavy metals such as lead. The surfactant wetting agent is used to moisten the dried collection paper to facilitate more rapid elution of the blood components into the resulting solution.

The solution eluted from the dried blood sample on the filter collection paper disks may also be used for analytical chemical measurement of trace amounts of other heavy metals. The eluted solution may be stable for up to four weeks when properly stored. The eluted solution may be tested directly for lead content of the blood sample. Testing may be performed by an atomic absorption spectrometer (AAS) system or any other well-known method of testing for atoms of heavy metals.

In one aspect of the present invention, the eluted blood and lead components may be centrifuged into a clear supernatant that is readily analyzed in a conventional atomic absorption spectrometer ("AAS") without the contamination and masking problems caused by constituent elements of the blood hemoglobin, blood protein and filter collection paper ash. The present invention is equally applicable in detecting trace amounts of other heavy metals such as, for example, selenium, mercury, and cadmium in microliters of dried blood.

The filter collection paper may be, for example, Schleicher & Schuell 903 Blood Collection Paper ("903 Paper"). The blood sample spotted on the filter collection paper is dried, placed in a suitable storage container such as, for example, a glassine envelope for delivery to a testing laboratory. The 903 Paper has the following characteristics:

SPECIFICATIONS FOR 903 COLLECTION PAPER

| Liquid Filtration Speed (sec) | Densometer (sec) | Precipitates Retained |
|---|---|---|
| TAPPI T471 | TAPPI T471 | ASTM D981-56 |
| u.m. 572 | u.m. 572 | 8–30 μm particles |
| ASTM E832-9.3 | ASTM 726 | |
| 7.3 sec | 20 sec | |
| Surface | Basis Weight ($g/m^2$) | Caliper (mm) |
| smooth; | TAPPI T471 | TAPPI T471 |
| not hardened | u.m. 572 | u.m. 572 |
| | TAPPI T 410 | TAPPI T411 |

-continued

SPECIFICATIONS FOR 903 COLLECTION PAPER

| Liquid Filtration Speed (sec) | Densometer (sec) | Precipitates Retained |
|---|---|---|
| | ASTM 646 | ASTM 643 |
| | 179 $g/m^2$ | 0.52 mm thickness |
| Water Absorbency | Klemm | Wet Strength/ |
| (g/100 cc) | (1/16"/min) | 5 Sheets |
| | | (psi) |
| TAPPI T441 | TAPPI T441 | TAPPI T471 |
| ASTM 3285 | ASTM 3285 | u.m. 572 |
| 4.5 g/100 cc | 34 | TAPPI T403 |
| | | ASTM 774 |
| | | 7.0 psi |
| Mean Serum Uptake | | |
| 1.52 μL/⅛" disc | | |

The 903 Paper effectively binds the blood hemoglobin and proteins so that the dilute acid only removes the blood parts containing the trace elements of lead.

At the testing laboratory, a predetermined area such as, for example, a half-inch diameter spot, may be removed from the filter collection paper by using a one-quarter inch diameter paper punch and punching about four to six segments from the filter collection paper. These segments are placed into a small test tube and a solution of one milliliter of five percent volume per volume nitric acid containing 0.75 percent volume per volume Triton X-100 (Registered Trademark of Rohm & Haas) is added thereto. Triton X-100 comprises one of a class of polyoxyethylene ethers. Other non-ionic polar surfactants (detergents) such as ethylene oxide-fatty alcohol condensates or diethylene glycol ethers may be used.

The filter collection paper segments and solution contained in the test tube are thoroughly mixed together by vortexing. After vortexing the filter collection paper and solution, the test tubes are allowed to stand for approximately 15 minutes, and then the test tubes are centrifuged for approximately 5 minutes. The resulting clear supernatant may be transferred to a storage container such as, for example, a plastic sample cup ready for testing in the AAS system.

The clear supernatant sample may be transferred directly to a graphite furnace used with the AAS and a spectral analysis run to determine the concentrations of lead in the blood sample. The system and method of the present invention may be calibrated with aqueous lead standards such as, for example, 50 milliliters diluted with 0.95 milliliter five percent volume per volume nitric acid and 0.75 percent Triton X-100®

An object of the present invention is to collect a capillary blood sample on conventional blood collection paper, allowing the blood sample to dry, and shipping the dried blood sample to a laboratory for testing.

Another object is to treat a predetermined volume of a dried blood sample contained on collection paper with a dilute aqueous acid reagent containing a surfactant wetting agent that produces substantially a protein free solution suitable for analysis of trace elements of lead in the blood.

Yet another object of the present invention is to produce a clear supernatant from the substantially protein free solution of blood parts containing traces of lead suitable for analytical chemical measurement of the trace elements.

Still another object is to measure trace elements in a blood sample such as lead, selenium, mercury, cadmium, chromium, nickel and beryllium.

An advantage of the present invention is that it is easier to obtain capillary blood samples than blood from the veins of small children or workers in a factory.

Another advantage is that the blood sample taken may be dried, stored and easily mailed to a laboratory for testing.

A further advantage is that the lead testing system may be calibrated with simple aqueous standards.

Still a further advantage of the present invention is that the blood protein free aqueous extract may be used in a graphite furnace without creating excessive carbonaceous residue build up therein, thus, prolonging the life of the graphite furnace.

Still another advantage is that the blood samples taken on the filter collection paper remain stable for at least six months without special storage requirements.

A feature of the present invention is the use of a calibrated area that can be punched to obtain consistent, representative, sample volumes of whole blood on the collection paper.

Another feature is the use of an aqueous solution that is free of hemoglobin and blood proteins and is suitable for direct analysis of heavy metals in a blood sample.

Other and further objects, features and advantages will be apparent from the following description from the presently preferred embodiment of the invention, given for the purpose of disclosure and taken in conjunction with the accompanying drawings.

DETAILED DESCRIPTION OF A PREFERRED EMBODIMENT

Figure 1:
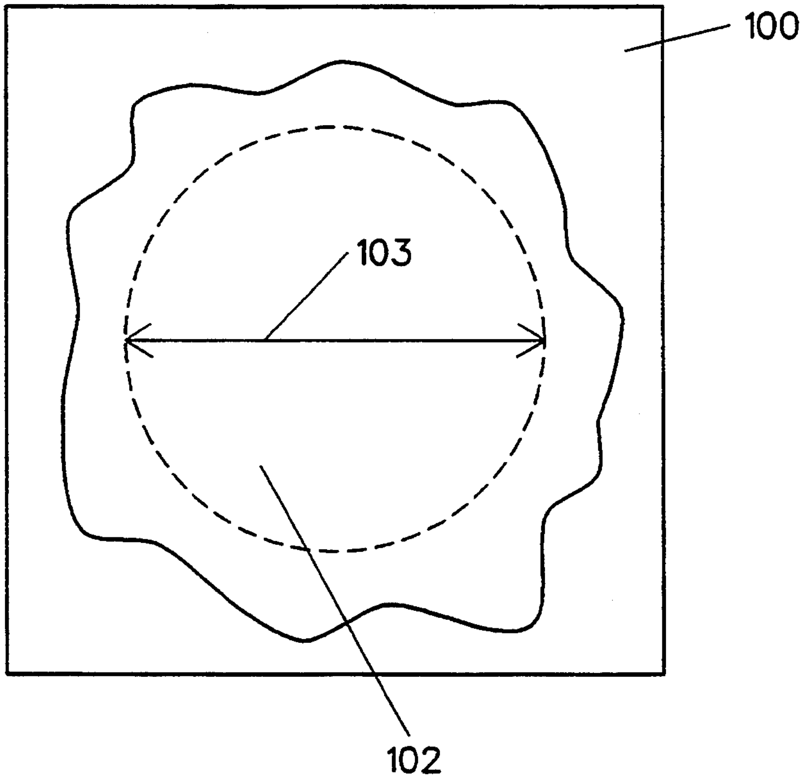
FIG. 1 illustrates a blood sample spot on collection paper according to an embodiment of the present invention.

Referring now to the drawings, the details of a preferred embodiment are schematically illustrated. Like elements are numbered the same, and similar elements are represented by the same number and a different lower case letter suffix. Referring now to FIG. 1, illustrated is a blood sample 102 that is deposited onto filter collection paper 100 in a spot pattern. The blood sample 102 is allowed to dry by means of air drying, use of a hair dryer, or at a low temperature of, e.g., 50° C. in an oven depending on how soon it is desired to test the blood sample 102 according to the present invention. The blood sample 102 has a diameter 103 of at least one-half inch.

Figure 2:
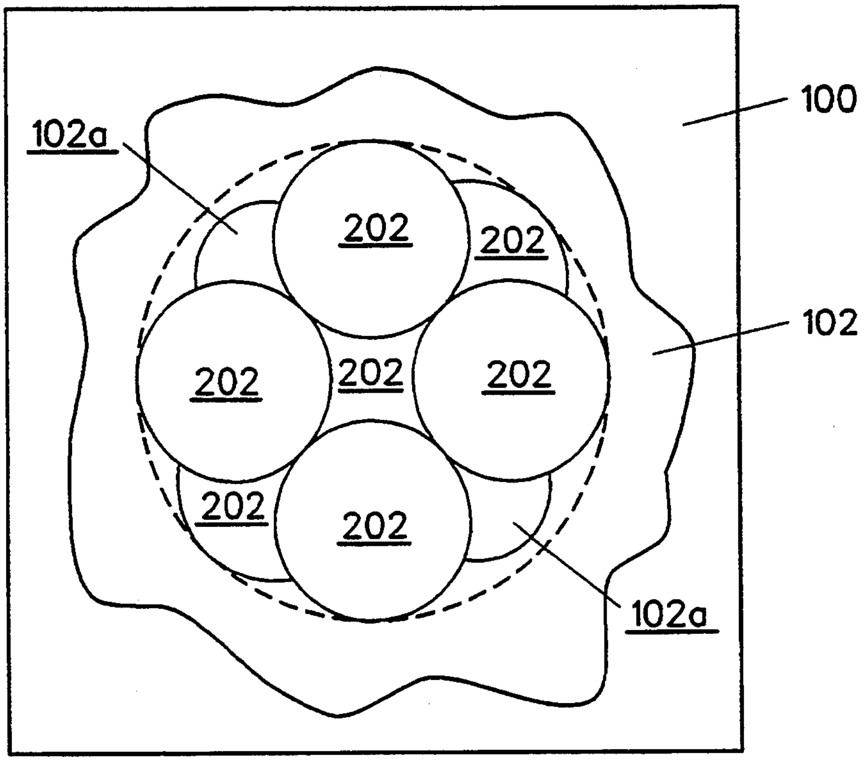
FIG. 2 illustrates the blood spot of FIG. 1 having four to six disks removed within a one-half inch diameter circle so as to define a predetermined volume of whole blood sample.

Referring now to FIG. 2, all disks 202 of the dried blood sample 102 within a one-half inch diameter circle are punched out. All the disks 202 within the one-half inch diameter circle result in a known volume of the blood sample **102*a*. By utilizing these predefined disks 202, a representative volume of the blood sample 102*a* is obtained for subsequent testing thereof. The dried blood sample 102 on the filter collection paper 100 may be stored for six months without substantial degradation. The filter collection paper 100** may also be easily stored and shipped to a testing laboratory in a glassine or paper envelope (not illustrated).

Figure 3:
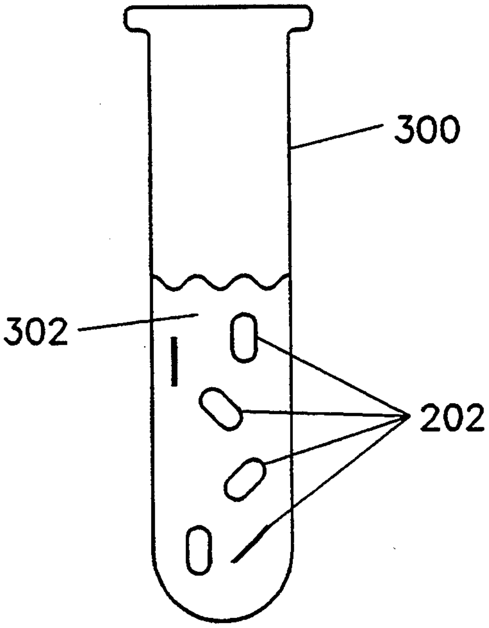
FIG. 3 illustrates a test tube containing the disks of FIG. 2 and the eluting solution of the present invention.

During preparation for testing, the disks 202 are punched out and placed in a test tube for further processing. Referring to FIG. 3, a test tube 300 is illustrated containing the disks 202 and an eluting solution 302. The eluting solution 302 is a dilute aqueous acid reagent containing a surfactant wetting agent. The eluting solution 302 may be comprised preferably of five percent volume per volume of nitric acid with 0.75 percent volume per volume of Triton X-100® (Triton X-100 is a registered trademark of the Rohm & Haas Company). Triton X-100 is a polyoxyethylene ether.

Figure 4:
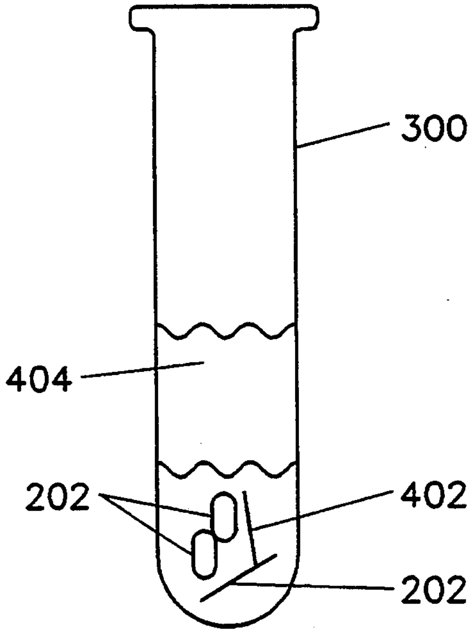
FIG. 4 illustrates the test tube and contents therein of FIG. 3 after vortexing and centrifuging.

The disks 202 are mixed with the eluting solution 302 preferably by vortexing until thoroughly mixed. After mixing, the test tube 300 is allowed to stand for preferably 15 minutes. Then the test tube 300 is placed in a centrifuge for preferably 5 minutes, wherein the eluting solution 302 and disks 202 separate into a particulate 402 and a clear liquid supernatant 404, as more fully illustrated in FIG. 4.

Figure 5A:
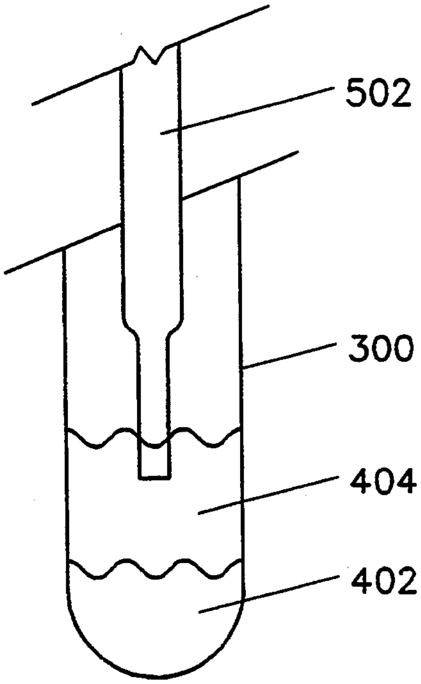
FIGS. 5A and 5B illustrate the transfer of the supernatant from the contents of the test tube of FIG. 4.
Figure 5B:
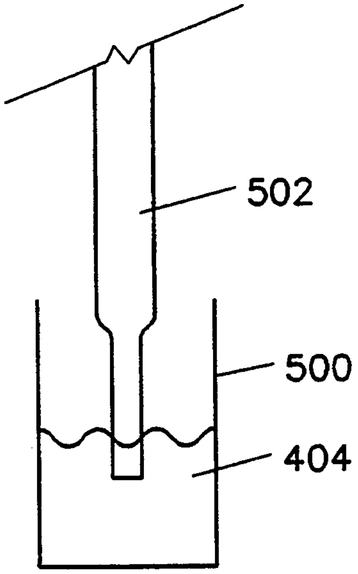
Figure 6:
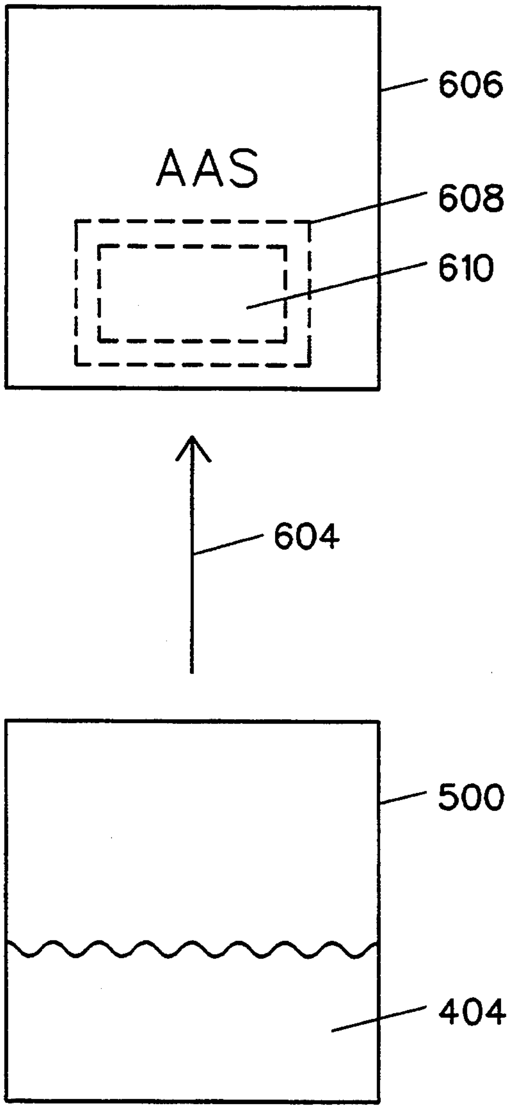
FIG. 6 illustrates an atomic absorption spectrometer system for determining heavy metal trace elements according to an embodiment of the present invention.

Referring now to FIGS. 5A and 5B, the supernatant 404 is removed from the test tube 300 by means of a pipette 502 or other means will known to those skilled in chemistry. The pipette 502 transfers the supernatant 404 to a sample cup 500. The sample cup 500 may now be utilized to either store the supernatant or, as more fully illustrated in FIG. 6, hold the supernatant 404 for use with an atomic absorption spectrometer 606.

After transferring an amount of supernatant required for analysis into the atomic absorption spectrometer graphite furnace 608, the supernatant 404 is heated to boil off (vaporize) liquid and to impart thermal energy to all of the molecules and atoms contained therein. The heated supernatant 404 vapor 604 passes between a lamp that emits spectral line energy (not illustrated) and a detector (not illustrated). The spectrometer 606 determines the difference in transmitted energy measured with and without atoms of the element of interest. AAS is well know to those skilled in the art of analytic chemistry trace element measurements. Other trace element analytic chemistry measurement methods may be similarly utilized.

The supernatant 404 of the present invention introduces less undesirable elements during the trace element testing. Thus, the graphite tube 610 is not contaminated with excessive residual carbon soot which greatly increases the useful life of this component. The constituent elements of the blood hemoglobin and protein, and the filter collection paper 100 are no longer present in the supernatant, thus, these unwanted materials cannot mask the desired spectral peaks found by the AAS which indicate the presence of trace heavy metals such as, for example, lead.

The system and method of the present invention, therefore, is well adapted to carry out the objects and attain the ends and advantages mentioned, as well as others inherent therein. While a presently preferred embodiment of the invention has been given for purposes of disclosure, numerous changes in the details of procedures for accomplishing the desired results, chemical combinations that perform the disclosed functions, and methods of testing will readily suggest themselves to those skilled in the art, and which are encompassed within the spirit of the invention and the scope of the appended claims.

What is claimed is:

1. A method for determining the amount of heavy metal trace elements in a blood sample, comprising the steps of:

spotting a blood sample on a filter collection paper;

drying the spotted blood sample on the collection paper;

removing a predefined area containing the dried blood sample from the collection paper;

placing the predefined area containing the dried blood sample into a solution of dilute aqueous acid reagent containing a surfactant wetting agent;

mixing the solution and the dried blood sample;

allowing the mixture of the dried blood sample and the solution to stand for a first predetermined time;

centrifuging the mixture for a second predetermined time;

removing a clear supernatant liquid from the mixture; and testing the clear supernatant liquid for traces of heavy metal elements.

2. The method of claim 1, wherein the step of mixing is by vortexing.

3. The method of claim 1, wherein the step of testing the clear supernatant for heavy metal trace elements is by an atomic absorption spectrometer.

4. A method for determining the amount of lead trace elements in a blood sample, comprising the steps of:

collecting a whole blood sample by means of a finger or earlobe prick;

spotting the collected blood sample on a filter collection paper;

drying the spotted blood sample on the filter collection paper;

punching out segments equaling approximately one-half inch diameter of the collection paper containing the dried blood sample;

placing the segments of the collection paper containing the dried blood sample into a test tube;

adding into the test tube approximately a 1.0 milliliter solution containing 5 percent volume per volume of nitric acid and 0.75 percent volume per volume of a non-ionic polar surfactant;

mixing the solution with the segments of the collection paper containing the dried blood sample;

allowing the mixture of the dried blood sample and the solution to stand for approximately 15 minutes;

centrifuging the mixture in the test tube for approximately 5 minutes;

removing a clear supernatant from the test tube; and testing the clear supernatant liquid for traces of lead with an atomic absorption spectrometer.

* * * * *